United States Patent [19]

Zander et al.

[11] Patent Number: 5,041,387

[45] Date of Patent: Aug. 20, 1991

[54] DETERMINATION OF THE ACID-BASE STATUS OF BLOOD

[76] Inventors: Rolf Zander, R.-Schneider-Strasse 1, 6500 Mainz; Hans U. Wolf, Liszt-Strasse 10, 7910 Neu-Ulm, both of Fed. Rep. of Germany

[21] Appl. No.: 882,638

[22] Filed: Jul. 7, 1986

Related U.S. Application Data

[60] Continuation of Ser. No. 595,986, Apr. 2, 1984, abandoned, which is a division of Ser. No. 364,665, Apr. 2, 1982, Pat. No. 4,454,229.

[30] Foreign Application Priority Data

Apr. 6, 1981 [DE] Fed. Rep. of Germany ....... 3113797

[51] Int. Cl.$^5$ .................................................. G01N 33/49
[52] U.S. Cl. ................................. 422/82.05; 422/73; 422/79; 436/62; 436/66; 436/68; 436/164
[58] Field of Search .................. 422/68, 73, 79, 99, 422/82.05; 436/62, 68, 66, 164

[56] References Cited

U.S. PATENT DOCUMENTS

| | | | |
|---|---|---|---|
| 2,951,689 | 9/1960 | Asp et al. | 422/99 X |
| 3,282,803 | 11/1966 | Poepel et al. | 436/62 |
| 3,492,396 | 1/1970 | Dalton et al. | 422/73 X |
| 3,973,915 | 8/1976 | Raffaele et al. | 436/68 X |
| 4,013,417 | 3/1977 | Raffaele | 436/68 X |
| 4,324,556 | 4/1982 | Robertson et al. | 422/68 X |
| 4,454,229 | 6/1984 | Zander et al. | 436/68 |
| 4,580,895 | 4/1986 | Patel | 422/73 |

FOREIGN PATENT DOCUMENTS

| | | | |
|---|---|---|---|
| 1354344 | 5/1974 | United Kingdom | 422/79 |
| 1533661 | 11/1978 | United Kingdom | 436/68 |

*Primary Examiner*—Jill Johnston
*Attorney, Agent, or Firm*—Michael J. Striker

[57] ABSTRACT

In order to simplify the operation for determination of the acid-base status of blood, composed of the values for pH, $pCO_2$ and the base excess BE, the base excess BE is determined through measurement of the pH-value at a $pCO_2$ of about 0 mn Hg. The pH-values may be determined photometrically, in which case the indicator solution for measuring the actual blood-pH is an aqueous solution of 40 micromol/l bromthymol blue plus 0.2 g/l sodium dodecylsulfate plus 1% ethanol; and for measurement of the base excess BE is an aqueous solution of 65 micro mol/l naphtholphthalein plus 0.2 g/l sodium dodecylsulfate plus 15% dimethylsulfoxide, which are measured at a wavelength of 635 nm. If desired, one may use a single solution for measuring both actual blood-pH as well as the base excess BE, composed of 16 micromol/l bromthymol blue plus 34 micromol/l naphtholphthalein plus 0.15 g/l sodium dodecylsulfate, which is measured at 615 nm wavelength.

2 Claims, 5 Drawing Sheets

DETERMINATION OF THE ACID-BASE STATUS OF BLOOD

This is a continuation of application Ser. No. 06/595,986, filed Apr. 2, 1984 and now abandoned, which in turn is a divisional application of application Ser. No. 06/364,665, filed Apr. 2, 1982, now U.S. Pat. No. 4,454,229.

BACKGROUND OF THE INVENTION

The invention concerns a method and an arrangement for the measurement of the acid-base status of blood, which embraces the determination of the pH, the $pCO_2$ and the base excess BE.

The metabolic processes in the human organism can take place without disturbance only within a relatively narrowly limited pH-range. For stabilization of this pH range, which lies, for example in blood plasma, between about 7.37 and 7.43, the organism has available a series of regulatory mechanisms based upon electrolytically active material systems, which through regulation of the amount of each of their particle fractions attempt to maintain the normal pH-value against disturbances to the normal metabolism or from pathological processes.

The two most important electrolytically active material systems are the $CO_2$-system on the one hand and the system of non-volatile bases, composed of phosphates and proteinates, on the other hand, which are active in the blood as pH-determining fractions. Both systems are coupled through the bicarbonate $HCO_3^-$, originating from $CO_2$, i.e. the volatile base, which forms the largest particle fraction.

It is now indeed possible without more to conceive through measuring techniques the pH-value of the blood plasma, which is representative of the pH-value of the organism. However, it is very laborious to provide the individual contributions to the pH-value, which originate from the proteinate-phosphate system (referred to hereafter as the PP-system), the $CO_2$-system or the bicarbonate system. Correspondingly, it is difficult to determine the measured variables pH, $pCO_2$ and the buffer base concentration BB or the base excess BE, standing in connection therewith, customarily designated as "acid-base status".

On account of the fundamental importance of the pH-value for the total metabolism, the acid-base status is a significant variable for diagnosis and choice of therapy.

The previous methods for determination of the acid-base status proceed from the law of mass action for the bicarbonate-carbonic acid system, as follows:

$$\frac{(H^+)(HCO_3^-)}{(H_2CO_3)} = K$$

which leads, through taking of logarithms, to the equation $$pH = pK + \log \frac{(HCO_3^-)}{0.03 * pCO_2}$$

according to the Henderson-Hasselbalch equation, when instead of the undissociated carbonic acid, the $CO_2$-partial pressure, i.e. $pCO_2$, is used.

Thereby a linear function is obtained, with logarithmic graduation of the coordinates, a linear function, which is representable in two dimensions. From this can be chosen either a pH-$HCO_3$-diagram with $pCO_2$ as parameter, a $pCO_2$-$HCO_3^-$-diagram with pH as parameter, or a pH-$pCO_2$-diagram with $HCO_3^-$ as parameter.

If one chooses, for example, the pH-$pCO_2$-diagram, then there results from each two pH-$pCO_2$ value pairs a line which belongs to a fixed $HCO_3$-value.

For the most part, in practice, the bicarbonate is not considered alone, but together with the proteinate-phosphate-system (PP). Both fractions together are customarily designated as "buffer bases" (BB).

To illustrate, FIG. 1 represents a diagram according to Astrup & Siggaard-Andersen, The Acid-Base Status of the Blood, Munksgaard, Copenhagen, 1974). There, the points A and B in the diagram are determined through equilibration of a blood sample with two $CO_2$-partial pressures corresponding to points A and B and through measurement of the attendant pH-value. The thereby determined titration line—also referred to as "equilibration line"—intersects the curve (BB) obtained through standardization. From the point of intersection can be read that in the blood sample, in addition to the pH-value determining $CO_2$ (variable along the equilibration line), a concentration of 37 milli-equivalents per liter of buffer bases is present. (Normal value: about 48.0 milliequivalents per liter; altering the content of buffer bases displaces the equilibration line roughly parallel.)

From the titration line, moreover, the actual $pCO_2$ can yet be found through measurement of the actual pH-value.

The cost of the measuring techniques for obtaining the value of the buffer bases is thus correctly high: one must prepare two precisely determined $CO_2$-gas-mixtures, and the blood sample must be held under physiological conditions, i.e. thermostatically controlled to avoid pH-thermodrift of the blood. Hemolysis must be excluded, since otherwise the erythrocytes, having a pH-value lying about 0.2 pH-units below the plasma-pH-value, alter the plasma-pH-value and thereby the measured values.

Likewise, the so-called "direct method" (Siggaard-Andersen, The Acid-Base Status of the Blood, Munksgaard, Copenhagen, 1974) is laborious.

SUMMARY OF THE INVENTION

It is therefore an object of the present invention to develop a method for the determination of the acid-base status of blood, which is simpler to perform than the previously known methods.

This object is attained according to the present invention by determining the base excess BE through measurement of the pH-value at a $pCO_2$ of about 0 mm Hg.

Such a method has many advantages:

A thermostatization is not necessary, since no measurements subject to thermodrift have to be done.

The hemolysis occurring upon equilibration of the sample indeed decreases the pH-value, but there is no longer produced therefrom an alteration of the $pCO_2$, since $CO_2$ is no longer present. It is only the absolute value of the pH which is displaced (which displacement can be mathematically eliminated), since in the erythrocytes a pH-value smaller by about 0.2 units is present.

The condition $pCO_2=0$ with oxygen saturation (standardization) of the blood is practically already present in the laboratory atmosphere, and does not first have to be produced with appropriate gas mixtures.

In addition, the error in measurement can be reduced by about a factor of 3: The titration lines lose their linearity at low $pCO_2$-values, and curve, from about 20 mm Hg $pCO_2$, growing towards the abscissa. This curvature follows all the sooner, the less buffer bases are dissolved in the blood. This leads with negligible $CO_2$-partial pressure to a fan-like spreading-out of the titration lines and an enlargement of the pH-difference for different concentrations of buffer bases of roughly about three times, compared to the pH-differences in the physiological range. Moreover, there occurs with this breaking of the logarithmic connection between pH and $pCO_2$, the stabilization technically necessary for measuring the final value.

A likewise technically effective advantage for measuring is that the BE-measurement now follows respiratorically neutral, since only the non-volatile PP-fraction is measured. Thereby is eliminated the indetermination which is produced through the bicarbonate as physiological regulating-and linkage-member between the PP-fraction and the $CO_2$-fraction.

To illustrate, a group of titration curves is represented in the pH-$pCO_2$-diagram in FIG. 2. The titration curve A is initially a line, which declines then in the lower range, relatively sooner than with higher $pCO_2$, downward away from the titration curve B, which declines sooner away from the titration curve C. The pH-differences are thus increased, and it is moreover clearly recognizable that the pH-value itself no longer changes at $CO_2$-partial pressures between 0 and about 1 mm Hg. Thereby also the adjustment of the pH-value is non-critical.

Instead of the concentration of buffer bases, the value for the base excess BE is specified. It represents the difference between the actual value of buffer bases (BB) and the normal value. (Normal: about 48.0 milliequivalents/l; with 150 g/l hemoglobin, complete $O_2$-saturation, 38° C.) The measurement follows in such manner that a blood sample of about 60 microliters is withdrawn, and divided into three equal parts of 20 microliters each. One part is used for determination of the actual pH, one part for determination of the BE-value after $CO_2$-outgassing, and one part for conventional Hb-determination for measuring Hb-concentration. From the actual pH-value, the BE-value as well as the Hb-value can be determined then the $pCO_2$-value, from one of the known nomograms or through calibration of the photometer itself, thereby thus determining the acid-base status of a blood sample.

One can thus satisfy the object according to the present invention through two measured values obtained by means of non-critical measuring techniques. The time spent amounts to about 3 minutes, inclusive of the equilibration period.

In a further embodiment of the method, the measurement of the pH follows photometrically.

This embodiment has the advantage that a problem-free photometric arrangement can be reached. This follows, though, contrary to prevailing technical opinions, which have previously essentially criticized photometric processes for the determination of the acid-base status as being too inaccurate. This way of thinking, however, no longer proves correct for the embodiment of the method according to the present invention.

Particularly good results can be obtained, when the indicator solution is,
for measurement of the actual blood-pH:
an aqueous solution of 40 micromol/l
bromthymol blue plus 0.2 g/l sodium
dodecyl sulfate plus 1% ethanol;
for measurement of the base excess BE:
an aqueous solution of 65 micromol/l
naphtholphthalein plus 0.2 g/l sodium
dodecylsulfate plus 15% dimethyl sulfoxide;
which are measured at a wavelength of 635 nm.

If it is desired to use a single indicator solution for both measurements, then the solution is advantageously composed of
16 micromol/l bromthymol blue plus
34 micromol/l naphtholphthalein plus
0.15 g/l sodium dodecylsulfate
and will be measured at 615 nm wavelength.

The advantage of these indicators is that the extinction maxima lie far above 600 nm, and therefore the extraordinarily high extinction of the blood—even with great dilution—no longer interferes. The sensitivity is so great that with good dissolution only small amounts of blood are necessary for the measured values. The change point lies within the range of measurements. The connection between extinction and pH-value is approximately linear. Since buffer effect of the indicators is small in contrast to the buffer capacity of the blood, the albumen error and the temperature deviation are negligible. The indicators are also well soluble in water.

The equilibration of the sample must be done with great attention when practicing the known methods. In contrast, the equilibration is unproblematical with the method according to the present invention. It is already facilitated in that the normal atmosphere displays a $CO_2$-partial pressure of only about 0.2 mm Hg. Since the atmosphere represents practically an infinitely large reservoir for this partial pressure, such measures which bring about a sufficient rate of diffusion for the $CO_2$ lead to a sufficient $CO_2$-equilibration.

It is thus of particular advantage when the equilibration of the blood follows through drying in the atmosphere, in thin layers, since thereby the apparatus and time expenditures for equilibration can be drastically reduced.

Beyond that, all arrangements are expedient, which provide means for shortening the diffusion distance in the blood sample inside a chamber, with additional binding agents for $CO_2$.

For example, it is advantageous to use an arrangement which displays magnetic stirring rods coated with polyamide of about 6 mm diameter and 10 mm length, which are rotatable in a stirring body of about 15 mm diameter, whereby the stirring body is disposed in a sleeve of aerated plastic, about 2 to 3 mm thick and soaked with 0.1 M NaOH, and which is completely separated from the atmosphere by means of a chamber.

Since this arrangement provides a good $CO_2$-absorption with simultaneously good oxygenation of the blood, without having the blood sample dry up, it is thus manipulated under partially physiological conditions.

It is however also possible to manipulate the sample under non-physiological conditions. For this the blood sample is allotted to glass balls. This increases the surface for the blood film very strongly, so that the sample dries quickly under agitation and can be oxygenated. It thereby gives up the total $CO_2$.

The novel features which are considered characteristic for the invention are set forth in particular in the appended claims. The invention itself, however, both as to its construction and its method of operation, together with additional objects and advantages thereof, will be best understood from the following description of specific embodiments when read in connection with the accompanying drawing.

Figure 1:
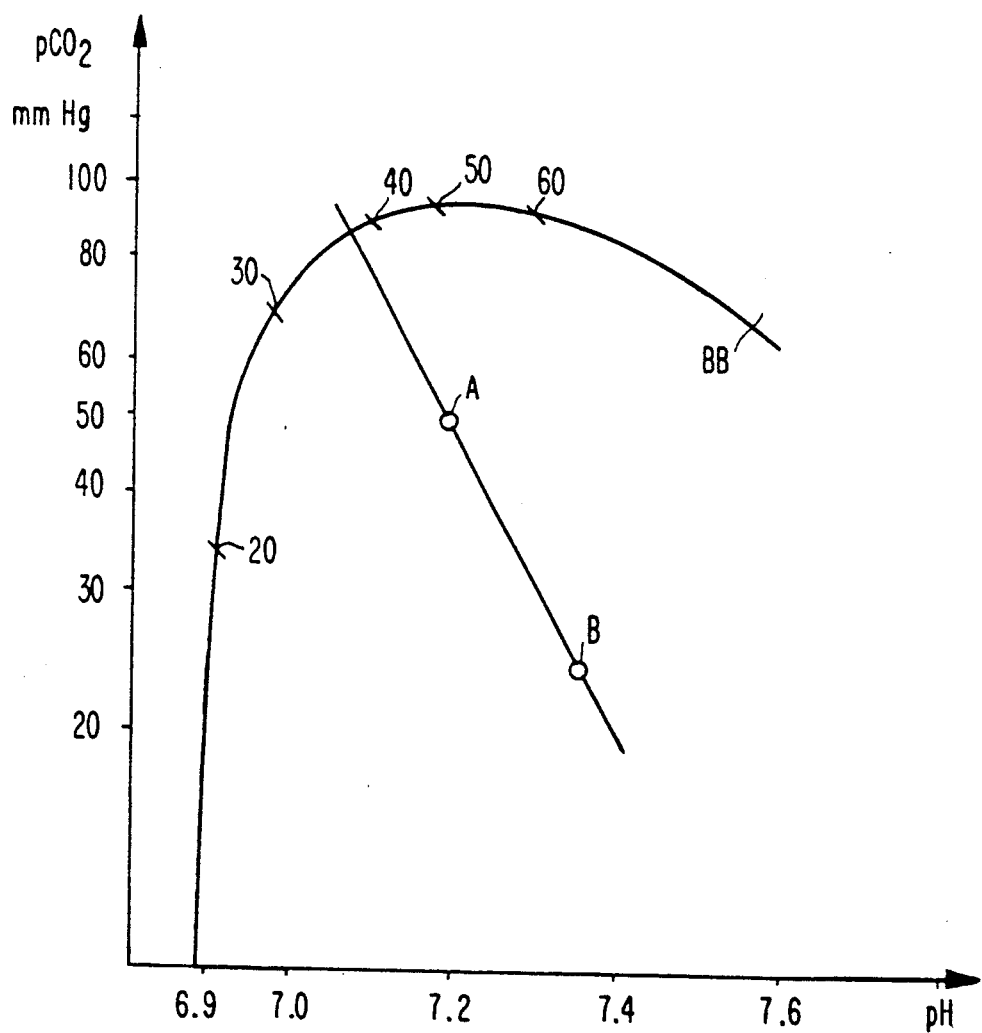
FIG. 1 is a diagram according to ASTRUP.
Figure 2:
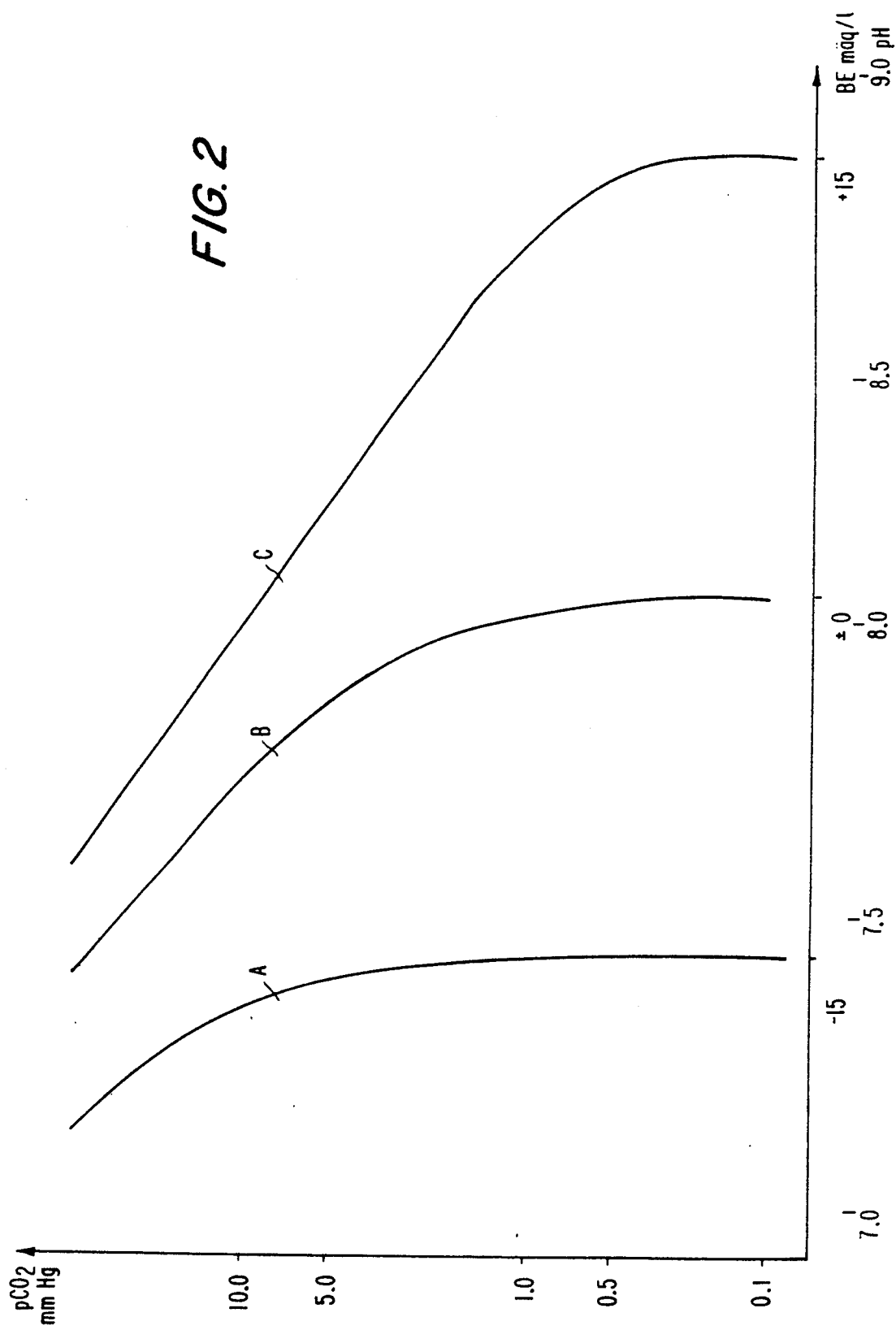
FIG. 2 is a pH-pCO$_2$-diagram for low pCO$_2$-values.

The diagrams in FIGS. 1 and 2 have already been discussed.

DESCRIPTION OF THE PREFERRED EMBODIMENTS

Figure 3:
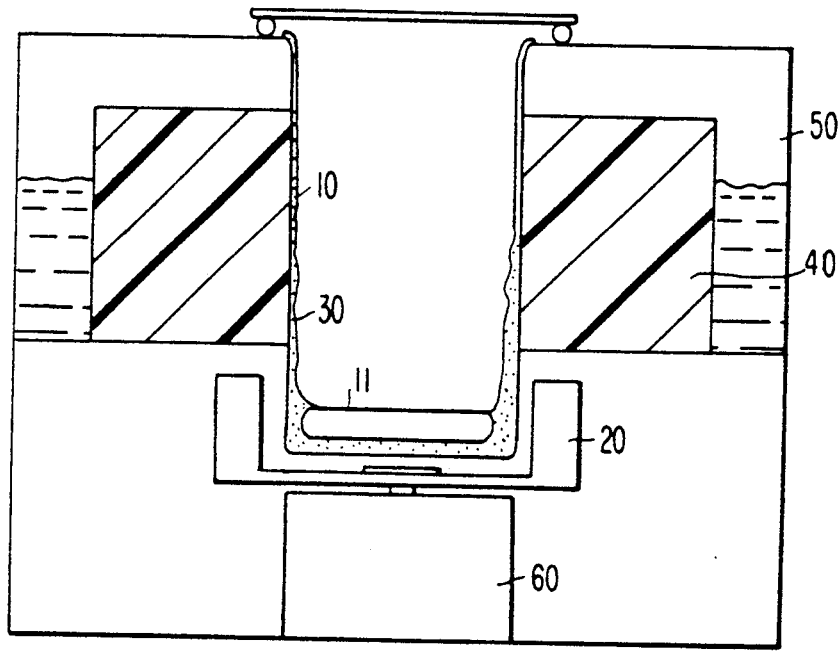
FIG. 3 is an arrangement for the equilibration to pCO$_2$=0.

In FIG. 3 there is represented a glass vessel 10 provided with a stirrer 11 coated with polyamide, which is set in rotation by a magnet 20 driven by a motor 60. The blood sample 30 is pushed high onto the wall of the glass vessel through centrifugal force upon motion of the stirrer 11, and presents thereby a large surface to the atmosphere in a chamber 50. Through a sleeve 40, of elastic aerated plastic and saturated completely with NaOH, the atmosphere in the chamber 50 is kept moist, but also free from CO$_2$, so that it can easily be put in equilibrium with the large surface of blood sample located on the glass wall.

If the motor 60 is operated in short time intervals, there follows moreover an intensive mixing of the blood sample and thereby collectively a fast equilibration.

The arrangement allows the equilibration of the blood under partially physiological conditions.

The equilibration under non-physiological conditions is simpler: For example, a blood sample of about 20 microliters and about 0.3 ml glass spheres of about 2 mm diameter are provided in a test tube, and the blood is dried under agitation. The result is a thin film of blood on the glass spheres, which is completely freed of CO$_2$ and oxygenated within about 1 to 3 minutes.

Figure 4:
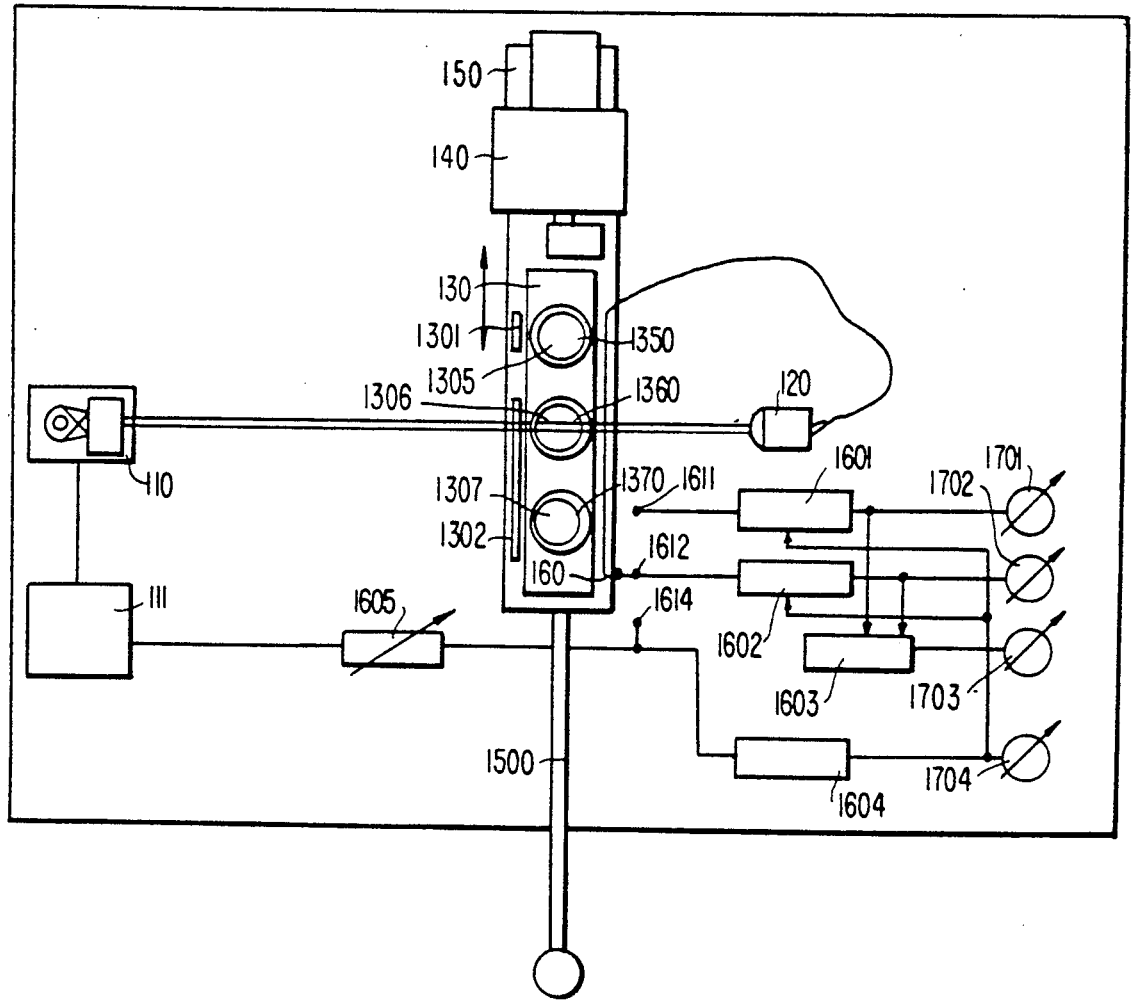
FIG. 4 is a measuring arrangement for the determination of the acid-base status of blood.

FIG. 4 represents schematically an arrangement for the complete determination of the acid-base status as well as the hemoglobin concentration. It can also be constructed without the arrangement for determination of hemoglobin, when the hemoglobin is already regularly provided from other measurements.

The described example embraces in the top view a light source 110 charged by a power supply 111, with a photoreceiver 120, in the path of the beam between which are provided a cell seat 130 with cell openings 1305, 1306 and 1307 for cells 1350, 1360 and 1370, and a filter 1301 for 575 nm wavelength to measure the hemoglobin concentration, as well as a filter 1302 of 635 nm for determination of the acid-base status. An agitating motor 140 is disposed on a displaceable base plate 150, which is movable in the path of the beam by means of the activation means 1500. The agitating motor agitates the cell seat together with the round cells put into the cell openings.

Figure 5:
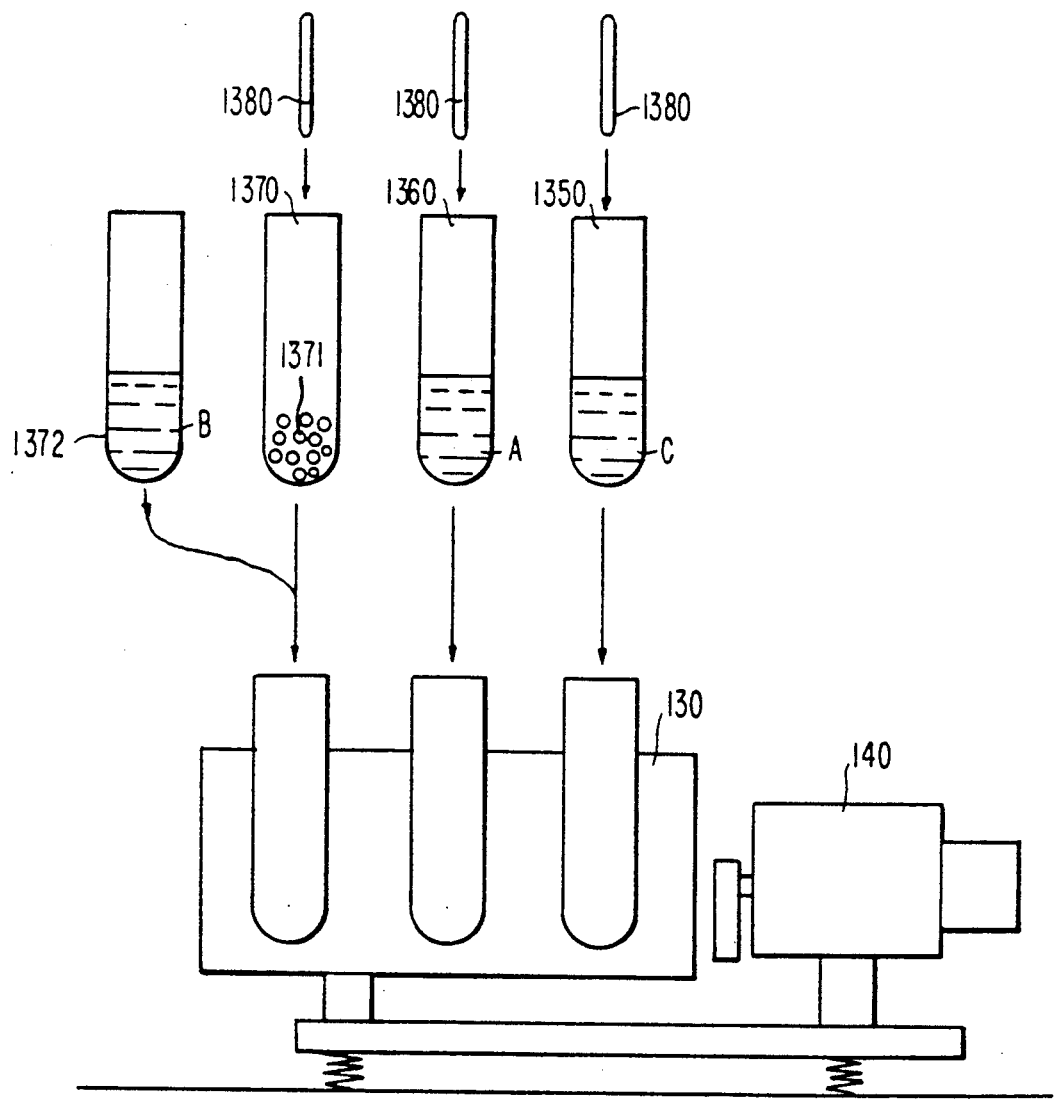
FIG. 5 is a side view of the cell seat.

In FIG. 5 is represented for illustration a side view of the cell seat 130 as well as the accompanying cells 1350, 1360, 1370 and 1372.

An analysis operation, using for example separate solutions for the pH and the BE measurements, has the following sequence: Three heparinised standard capillaries 1380 containing 20 microliters of blood each, are emptied:

a. one into a round cell 1370 filled with about 0.3 ml glass spheres of about 2 mm diameter;

b. one into a cell 1360 filled with 1.5 ml of a solution A;

c. one into a cell 1350 filled with 3.0 ml of a solution C.

d. The cell 1372 is filled with 1.5 ml solution B.

The solution A has the following composition:
an aqueous solution of 40 micromol/l bromthymol blue plus 0.2 g/l sodium dodecylsulfate plus 1% ethanol.

The solution B has the following composition:
an aqueous solution of 65 micromol/l naphtholphthalein plus 0.2 g/l sodium dodecylsulfate plus 15% dimethyl sulfoxide The solution C has the following composition:
0.1 M NaOH plus 2.5% TRITON X-100 (decaethyleneglycol-p-t-octylphenylether)

The arrangement is then agitated for about 20 seconds. This dries the blood in cell 1370 on the surface of the glass spheres 1371 to a very thin film, which, through the lively movement of the spheres in the atmosphere, leads to a fast equilibration with the CO$_2$-partial pressure of the atmosphere. The carbon dioxide partial pressure of the atmosphere of about 0.2 mm Hg together with the unlimited reservoir (for the measurement) as well as the oxygen partial pressure of 150 mm Hg are ideal standard conditions for equilibration.

After about 3 minutes, the cell 1372 filled with solution B is emptied into cell 1370 containing the glass spheres and the blood. The blood film located on the glass spheres is dissolved, advantageously with the aid of agitation, and the necessary three measurements of Hb, BE and pH can quickly be performed within a few seconds.

If it is desired to take the measurements with only a single solution, then solutions A and B are replaced by solution D, and filter 1302 is replaced by a filter for 615 nm. The solution D has the following composition:

16 micromol per liter bromthymol blue plus 34 micromol per liter naphtholphthalein plus 0.15 g/l sodium dodecylsulfate;

and is measured at 615 nm.

The arrangement can also be constructed without an agitating motor, since the cells can, without more, be agitated for a few seconds by hand.

A switch 160 is connected with the base plate 150, to effect distribution of the signal from photoreceiver 120 into the measuring positions 1611, 1612 and 1614 of the electrical function amplifiers 1601, 1602 and 1604.

The value for the hemoglobin concentration is determined with cell 1350 by means of the function $Fd=Fd(E3)$ from the extinction $E3$, and it is displayed by the indicator 1704.

The function Fd has the following form:

$$Fd: <Hb> = 34.95 E3$$

If the hemoglobin value is ordinarily known from other measurements, it can be adjusted with the aid of a potentiometer and presented as auxiliary voltage, whereby the costs of measuring the Hb are reduced. Then, however, the potentiometer 1605 must be set to a voltage corresponding to the particular Hb-value.

The functional amplifier 1601 forms the actual pH-value of the blood from the extinction value $E1$ of cell 1360 and the value for the hemoglobin concentration Hb by means of the function Fa=Fa(El,Hb), and it is displayed by the indicator 1701.

The function Fa has the following form:

$$Fa: pH = 6.2 + 0.0059 <Hb> + 1.6 E1.$$

The function amplifier 1602 forms the value of the base excess BE from the extinction value E2 of cell 1370 and the Hb value by means of the functions Fbi=Fbi(E2,Hb), and it is displayed by the indicator 1702.

The functions Fbi form a family of functions with Hb as parameter. The parameter values Hb=12 g/dl; 15 g/dl; and 18 g/dl give, for example, the following functions:

$$Fb1: BE = 0.929 E2^2 + 30.24 E2 - 20.47 <Hb=12\ g/dl>$$

$$Fb2: BE = -12.96 E2^2 + 48.82 E2 - 22.72 <Hv=15g/dl>$$

$$Fb3: BE = -26.84 E2^2 + 67.38 E2 - 24.97 <Hv=18g/dl>$$

Further functions Fbi can be determined as needed through interpolation from these values.

From the values pH, BE and Hb, a function amplifier 1603 forms the actual carbon dioxide partial pressure $pCO_2$ according to the function Fc=Fc(pH,BE,Hb), and this is displayed by the indicator 1703.

The values for Fc are to be withdrawn from one of the known (ph-BE-Hb)-$pCO_2$ nomograms, and are electronically storable in function amplifier 1603.

It will be understood that each of the elements described above, or two more together, may also find a useful application in other types of blood measurements differing from the types described above.

While the invention has been illustrated and described as embodied in a method and apparatus for the determination of the acid-base status of blood, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. Apparatus for the determination of the acid-base status of blood, using values for pH, $P_{CO_2}$ and base excess BE, by determining base excess BE through measurement of the pH-value at a $P_{CO_2}$-value at approximately 0 mm Hg, comprising:
   means for shortening a distance of diffusion in a sample of blood inside a chamber, provided with binding agents for $CO_2$; and
   glass spheres which are added to said sample of blood.

2. Apparatus for the determination of the acid-base status of a blood sample, using values for pH, $P_{CO_2}$ and the base excess BE through measurement of the pH value at a $P_{CO_2}$ value at approximately 0 mm Hg, comprising:
   a photometer displaying several measuring positions, said measuring positions corresponding to different display means, said display means displaying function amplifiers which provide signal influences necessary in the several measuring positions, wherein for a first measuring position for determination and display of the Hb-value, a function amplifier is provided with a function Fd of the form $$Fd: <Hb> = 34.95 E3;$$

in a second measuring position for determination and display of the BE-value, a function amplifier is provided with functions Fbi of the form $$Fb1: BE = 0.929 E2^2 + 30.24 E2 - 20.47 \text{ for } Hb=12g/dl$$

$$Fb2: BE = -12.96 E2^2 + 48.82 E2 - 22.72 \text{ for } Hb=15g/dl$$

$$Fb3: BE = -26.84 E2^2 + 67.38 E2 - 24.97 \text{ for } Hb=18g/dl$$

which are variable according to the function Fd; in a third measuring position for determination and display of the pH-value, a function amplifier is provided with a function Fa of the form $$Fa: pH = 6.2 + 0.0059 Hb + 1.6 * E1$$

which is variable according to the function Fd; and a function amplifier is provided, which for determination and display of the actual $P_{CO_2}$ combines the values pH, BE and Hb according to a (pH-BE-Hb)-$P_{CO_2}$ monogram, wherein, E1, E2 and E3 represent an extinction value for a first cell, a second cell and a third cell, respectively, each of said cells to contain a portion of the blood sample being tested.

* * * * *